United States Patent [19]

Angers

[11] Patent Number: 4,618,494
[45] Date of Patent: Oct. 21, 1986

[54] HUMAN IMMUNE FACTORS AND PROCESSES FOR THEIR PRODUCTION AND USE

[75] Inventor: John W. Angers, Red Bank, N.J.

[73] Assignee: Immunology Development Corporation, Red Bank, N.J.

[21] Appl. No.: 632,705

[22] Filed: Jul. 20, 1984

[51] Int. Cl.$^4$ .............................................. A61K 35/14
[52] U.S. Cl. ..................................... 424/101; 424/88; 424/89; 424/92; 424/85; 424/86; 424/87; 435/2
[58] Field of Search ...................... 435/2; 424/101, 88, 424/89, 92, 85, 86, 87

[56] References Cited

U.S. PATENT DOCUMENTS 4,085,204  4/1978  Wacker et al. ....................... 424/101
4,132,776  1/1979  Jeter ..................................... 424/101
4,468,379  8/1984  Gottlieb .............................. 424/101

OTHER PUBLICATIONS

Stiller et al., "Effects of Cyclosporine Immunosuppression in Insulin-Dependent Diabetes Mellitus of Recent Onset", *Science*, vol. 223, pp. 1362–1367, (Mar. 1984).

Duffy, Vaccine Preparation Techniques, (1980), pp. 281–287.

Induction of Tuberculin Type Hypersensitivity (Self Plus X), Hypothesis.

Lawrence, Recent Advances in the Immunotherapy of Infectious Diseases with Transfer Factor.

*Primary Examiner*—Sam Rosen

[57] ABSTRACT

Type 1 Diabetes and other virus-induced or autoimmunological diseases are treated with Human Immune Factors. These Human Immune Factors are extracted from blood cells by activating said blood cells with human lymphoblastoid interferon-alpha or staphage lysate or other activator or combination of activators. Human Immune Factors are purified and made suitable for pharmaceutical use by isolating compounds with molecular weights between about 1,000 and about 25,000 daltons.

37 Claims, No Drawings

HUMAN IMMUNE FACTORS AND PROCESSES FOR THEIR PRODUCTION AND USE

BACKGROUND OF THE INVENTION

This invention relates, in part, to therapeutic compositions which exhibit unexpected effectiveness in the treatment of certain virus-induced and autoimmunological medical disorders. The process for the preparation of such therapeutic compositions and the treatment of disease therewith are also included within the scope of the invention.

The present invention, while of general application, has proven particularly effective in the treatment of Type 1 Diabetes Mellitus. This disease is also known as "Juvenile Onset Diabetes Mellitus" or "Insulin Dependent Diabetes Mellitus" and will hereinafter be referred to as "Type 1 Diabetes". The disease is characterized by the destruction of pancreatic beta cells which normally produce and secrete the sugar regulatory hormone insulin. It is believed that compositions in accordance with the invention, when introduced into the bloodstream of Type 1 diabetics, effectively attenuate beta cell destruction. When Type 1 Diabetes is diagnosed before substantial beta cell destruction has taken place, a patient may avoid dependency on external source insulin by undergoing treatment with the therapeutic compositions of the instant inventions. Through such treatment, it is believed that the pancreatic beta cells are preserved such that they can continue to produce and secrete natural insulin thereby regulating body sugar levels.

In addition to the attendant significant discomfort, inconvenience and cost to a patient dependent on external source insulin, Type 1 Diabetes has also been found to lead to a multitude of other serious disorders resulting from sugar imbalances which cannot be completely controlled using external source insulin. Stiller et al. report in *Science*, volume 223 (1984) at page 1362 that the mortality rate of Type 1 diabetics is abnormally high four decades after the initial diagnosis is made. They also report an uncommonly high frequency of blindness, gangrene, and strokes.

It is widely believed that Type 1 Diabetes is caused by a virus or an autoimmune response possibly triggered by a virus. (See, for instance, Cudworth, Andrew G. and Andrew N. Gorsuch, "Autoimmunity and Viruses in Type 1 (Insulin-Dependent) Diabetes", *Diabetes Mellitus, Theory and Practice* (third ed. 1984), pp. 505-517.) Because of mounting evidence that beta cell destruction is caused by an autoimmune response, researchers have been led to working with immunosuppressants to determine their effectiveness in arresting beta cell destruction and restoring acceptable levels of endogenous insulin production.

In their *Science* article referred to above, Stiller et al. reported the testing of the immunosuppressive agent *Cyclosporine* on recently diagnosed Type 1 Diabetics. An encouragingly significant percentage of patients, especially those for whom treatment had begun very shortly after diagnosis, achieved independence from external source insulin. Unfortunately, use of *Cyclosporine* was also observed to cause serious undesirable side effects resulting from immunosuppression such as pancytopenia, cirrhosis of the liver, and loss of hair.

Others have employed *antithymocyte sera* to suppress beta cell destruction but with only weak responses. More conventional treatments for Type 1 Diabetes, the most common of which is the introduction of externally produced insulin, merely offset some of the undesirable consequences of the disease and are not successful in arresting the disease process. Additionally, external source insulin must be injected daily and, as a result, causes the patient great discomfort and is expensive.

It is an object of the invention to provide therapeutic compositions effective in the treatment of virus-induced and autoimmune diseases and a process for their preparation.

It is also an object of the present invention to provide a therapeutic composition effective in attenuating and arresting the destruction of pancreatic beta cells.

Another object of the invention is to provide a therapeutic composition for the treatment of Type 1 Diabetes with few, or no, undesirable side effects.

A further object is to provide a treatment for Type 1 Diabetes and other diseases, which is economical, convenient, and reliable.

STATEMENT OF THE INVENTION

The therapeutic compositions of the present invention basically comprise highly purified extracts of activated blood cells called "Human Immune Factors".

In order to produce the compositions of the invention, blood is withdrawn from a donor by one of the known methods. Donors are preferably relatives of the patient or individuals living in close contact with the patient. It has been found that the Human Immune Factors extractable from the blood cells of such donors are more likely to suppress the patient's particular disease process than are extracts from blood cells of randomly selected donors. However, extracts from blood cells of randomly selected donors have nonetheless proven effective. Furthermore, the blood need not be human blood since that of other mammals can also produce desired extracts.

The collected blood is mixed with a suitable activator which causes certain types of blood cells to secrete the extracts which are here called Human Immune Factors. Preferred activators include interferons such as human lymphoblastoid interferon-alpha or bacterial antigens such as staphage lysate, or other biological response modifiers. Combinations of two or more of such activators have been found to be particularly effective.

Because the secretion of Human Immune Factors is gradual, it is desirable to allow a substantial incubation period so that larger quantities can be obtained. The Human Immune Factors, once secreted, exist in admixture with blood and added activators. The Human Immune Factors are isolated from other compounds by known methods designed to retain only those compounds whose molecular weights fall between predetermined limits. Human Immune Factors are effectively isolated by retaining compounds with molecular weights between about 1,000 and about 25,000 daltons. Because interferon and other activators, as well as blood cells, antigens, and antibodies, typically all have molecular weights in excess of 25,000, they are removed by the process of the invention. Because HLA antigens are also removed, standard blood typing procedures are unnecessary and Human Immune Factors may be universally administered to patients of any blood type. It has been found that the most effective Human Immune Factors are obtained by using 1,000 daltons as the lower molecular weight limit and 10,000 to 14,000 daltons as the upper limit. Human Immune Factors with molecular weights between about 14,000 and about 25,000 daltons have been found to produce strong responses in some cases where the 1,000 to 14,000 dalton Human Immune Factors did not produce desired results. Thus these heavier Human Immune Factors represent a desirable alternative treatment in appropriate cases.

Human Immune Factors produced in accordance with the present invention are effectively administered on a weekly or bimonthly basis to patients suffering from various virus-induced or autoimmunological diseases.

It has been found that Human Immune Factors can be frozen without loss of potency for periods over two years and can be thawed and refrozen repeatedly without loss of potency. It has further been found that the compositions are not antigenic.

DESCRIPTION OF CERTAIN PREFERRED EMBODIMENTS

In a preferred embodiment of the invention, a patient to be treated suffers from Type 1 Diabetes which has recently been diagnosed while still in the early stages of pancreatic beta cell destruction. Other diseases which have proven particularly susceptible to treatment with Human Immune Factors include but are not limited to other forms of diabetes mellitus, primary immunodeficiency states characterized by impaired T-cell activities, infections, malignancy, psoriasis; multiple sclerosis, viral eye disease, respiratory disease, asthma, asthmatic bronchitis, and arthritis.

A relative of the patient, preferably one living in close contact with the patient, is chosen as a donor of whole blood. Routine blood banking tests are conducted to determine the healthiness of the donor and his blood. Approximately 500 milliliters of whole blood is collected from the donor and the donor's blood is preferably allowed to drain into blood collecting packs containing an appropriate anticoagulent such as heparin or citrate phosphate dextrose.

The cells in the collected blood are then activated by injecting directly into the blood pack $2.0 \times 10^5$ to $2.5 \times 10^5$ International Units of human lymphoblastoid interferon-alpha or 1 to 2 ml. of staphage lysate, or both. The resultant activated blood mixture is then incubated at approximately 37° C. for 24 to 48 hours. Longer incubation can be beneficial but is not essential. The mixture can then be subjected to dialysis and ultrafiltration to isolate Human Immune Factors, or it can be frozen at $-40°$ C. to $-10°$ C. until ready for use. If it is frozen, then the mixture should be thawed at room temperature before isolation of Human Immune Factors is begun.

Before proceeding with the isolation of Human Immune Factors, it is preferable to add a surfactant or wetting agent to prevent a portion of the extract from clinging to the walls of containers and thereby being lost during subsequent steps of the process. One suitable surfactant by way of example is polyoxyethylene sorbitan monooleate.

The mixture is then introduced into a dialysis membrane approximately 2.5 cm in diameter and with a molecular weight cutoff of from 10,000 to 14,000 daltons. The filled dialysis membrane is washed three times with a solution of 10% ethyl alcohol and deionized water and placed in a sterile Erlenmeyer flask. The ends of the dialysis membrane are kept out of the flask to prevent contamination with the whole blood. Approximately 2,000 ml of deionized water is added to the flask such that the deionized water is on the opposite side of the dialysis membrane from the whole blood. The blood mixture is then dialyzed with stirring at about 4° C.–10° C. for approximately 24 hours. After 24 hours, the dialysate is replaced with fresh deionized water and the membrane contents are allowed to dialyze for an additional period of approximately 24 hours. The original dialysate is retained and added to the dialysate obtained during the second 24 hour period. The combined dialysate contains the Human Immune Factors. The retentate (non dialysate) of this dialysis contains blood cells, compounds used as activators, HLA antigens, antibodies, and other unwanted contaminants. Thus the retentate is discarded.

The dialysate is concentrated by being poured into a stirred cell into which an ultrafiltration membrane with a molecular weight cutoff of approximately 1,000 daltons has been inserted. Approximately fifty pounds per square inch of pure nitrogen is used to propel the eluate (compounds with molecular weights below 1,000 daltons including undesirable immuno-inhibitors which could cause side effects) through the ultrafiltration membrane. The retentate of this process contains Human Immune Factors with a molecular weight in the desired range of 1,000 to 14,000 daltons. The eluate is discarded.

It is desirable to resuspend the retentate in an approximately 0.14 molar saline solution containing approximately 1.75% ethyl alcohol by volume. This solution is added only in amounts necessary to resuspend solidified Human Immune Factors. The resultant solution exists at a pharmaceutically desirable concentration for administration to patients. Other concentrations which might be desirable for particular uses can be obtained by adding either more or less of the saline/ethanol solution as required.

The resuspended Human Immune Factors are then administered to the newly diagnosed Type 1 Diabetic. The composition can be administered in a variety of ways including orally or by subcutaneous injection. The most effective results have been obtained by administering Human Immune Factors to the patient at least once every two weeks. Preferred dosages range from 2 to 5 ml per week of concentrated Human Immune Factors solution. Similar dosages are effective in treating other virus-induced or autoimmunological diseases.

EXAMPLES

Example 1

A solution of Human Immune Factors was prepared by draining 500 ml of a donor's blood into collecting packs containing citrate phosphate dextrose as an anticoagulent. $2 \times 10^5$ International Units of Human Lymphoblastoid Interferon-alpha was injected directly into the blood pack. The activated blood was then incubated at approximately 37° C. for two hours, after which 2 ml of Staphage Lysate was injected into the blood pack. The blood was then incubated at approximately 37° C. for 24 additional hours. 0.125 ml of polyoxyethylene sorbitan monooleate was added and the mixture was introduced into a dialysis membrane 2.5 cm in diameter with a molecular weight cut off of approximately 14,000 daltons. The filled dialysis membrane was washed three times with a solution of 10% ethyl alcohol and deionized water and placed in a sterile Erlenmeyer flask keeping the ends of the membrane out of the flask. 2,000 ml of deionized water was added to the flask, and the blood mixture was dialized with stirring at 4° C. for 24 hours. After 24 hours the dialysate was replaced with fresh deionized water and the membrane contents were allowed to dialize at 4° C. for another 24 hours. The dialysate of the second 24 hour period was then added to the dialysate of the first 24 hour period and both were poured into a two liter stirred cell into which an ultrafiltration membrane with a molecular weight cut off of approximately 1,000 daltons had been inserted. The cell was then pressurized with 50 pounds per square inch of pure nitrogen, and the mixture was stirred constantly under this pressure for more than 24 hours until less than 50 ml of retentate remained. The retentate was then resuspended by addition of an approximately 0.14 molar saline solution containing approximately 1.75% ethyl alcohol by volume in an amount sufficient to yield a final volume of 50 ml.

Example 2

A concentrated solution of Human Immune Factors prepared in accordance with the present invention was administered to a newly diagnosed Type 1 Diabetic on a weekly basis. Dosages administered ranged from 2 to 4 ml per week and response to this treatment was measured over a period of three months. A condition in which no insulin was required was attained by the patient notwithstanding that the patient had previously required treatment with external source insulin. Additionally, two measures of endogenous insulin production returned to normal. That is, both C-Peptide and Hemoglobin AlC levels returned to within the normal range and remained there at the end of the three month observation period. No undesirable side effects were documented.

The above examples are set forth in illustration of this invention and should not be construed as limitations thereof. The terms and expressions employed are used as terms of description and not as terms of limitation. There is no intention, in the use of such terms and expressions, of excluding any equivalents of the features described or portions thereof, it being recognized that various modifications are possible within the scope of the invention claimed.

I claim:

1. A process for the preparation of a pharmaceutical composition for treating virus-induced and autoimmune diseases which comprises:
   a. removal of a blood sample from a donor,
   b. treatment of the blood sample with at least one effective activator selected from the group of interferons, bacterial antigens or both, to form an activated blood mixture,
   c. incubation of the activated blood mixture for a period sufficient for blood cells in the blood mixture to secrete extracts,
   d. purification of the extracts from the activated blood mixture by isolation of compounds in the activated blood mixture with molecular weights in the range from about 1,000 to about 25,000 daltons.

2. The process of claim 1 wherein purification of the extracts is by dialysis and ultrafiltration.

3. The process of claim 1 wherein the activator is human lymphoblastoid interferon-alpha or staphage lysate or both.

4. The process of claim 1 wherein the incubation period is from about 24 to about 48 hours.

5. The process of claim 1 wherein purification isolates compounds having a molecular weight in the range of from about 1,000 to about 10,000 daltons.

6. The process of claim 1 which further comprises resuspending the purified extract in solution.

7. The process of claim 6 wherein the purified extract is resuspended in a solution of saline and ethyl alcohol.

8. The process of claim 6 wherein the purified extract is resuspended in approximately 0.14 molar saline solution containing approximately 1.75% ethyl alcohol by volume.

9. The process of claim 1 wherein the donor is a relative of the patient to be treated with the composition or is a member of the patient's household.

10. The process of claim 1 wherein purification isolates compounds having a molecular weight in the range of from about 1,000 to about 14,000 daltons, and wherein the activator is selected from the group of interferon, bacterial antigens, or both.

11. The process of claim 10 wherein the activator is human lymphoblastoid interferon-alpha or staphage lysate or both.

12. The process of claim 1 wherein purification isolates compounds having a molecular weight in the range of from about 14,000 to about 25,000 daltons, and wherein the activator is selected from the group of interferons, bacterial antigens, or both.

13. The process of claim 12 wherein the activator is human lymphoblastoid interferon-alpha or staphage lysate or both.

14. A pharmaceutical composition obtained by the process defined in claim 1.

15. A pharmaceutical composition obtained by the process defined in claim 3.

16. A pharmaceutical composition obtained by the process defined in claim 10.

17. A pharmaceutical composition obtained by the process defined in claim 11.

18. A pharmaceutical composition obtained by the process defined in claim 12.

19. A pharmaceutical composition obtained by the process defined in claim 13.

20. A method for the treatment of virus-induced or autoimmunological diseases which comprises administering an effective amount of the pharmaceutical composition defined in claim 14.

21. A method for the treatment of virus-induced or autoimmunological diseases which comprises administering an effective amount of the pharmaceutical composition defined in claim 15.

22. A method for the treatment of virus-induced or autoimmunological diseases which comprises administering an effective amount of the pharmaceutical composition defined in claim 16.

23. A method for the treatment of virus-induced or autoimmunological diseases which comprises administering an effective amount of the pharmaceutical composition defined in claim 19.

24. A method for the treatment of virus-induced or autoimmunological diseases which comprises administering an effective amount of the pharmaceutical composition defined in claim 18.

25. A method for the treatment of virus-induced or autoimmunological diseases which comprises administering an effective amount of the pharmaceutical composition defined in claim 19.

26. A method for the treatment of Type 1 Diabetes which comprises administering an effective amount of the pharmaceutical composition defined in claim 14.

27. A method for the treatment of Type 1 Diabetes which comprises administering an effective amount of the pharmaceutical composition defined in claim 15.

28. A method for the treatment of Type 1 Diabetes which comprises administering an effective amount of the pharmaceutical composition defined in claim 16.

29. A method for the treatment of Type 1 Diabetes which comprises administering an effective amount of the pharmaceutical composition defined in claim 17.

30. A method for the treatment of Type 1 Diabetes which comprises administering an effective amount of the pharmaceutical composition defined in claim 18.

31. A method for the treatment of Type 1 Diabetes which comprises administering an effective amount of the pharmaceutical composition defined in claim 19.

32. A method for the treatment of one or more virus-induced and autoimmune diseases selected from the group consisting of: diabetes mellitus, psoriasis, multiple sclerosis, viral eye disease, asthma, asthmatic bronchitis, and arthritis; which comprises administering an effective amount of the composition defined in claim 14.

33. A method for the treatment of one or more virus-induced and autoimmune diseases selected from the group consisting of: diabetes mellitus, psoriasis, multiple sclerosis, viral eye disease, asthma, asthmatic bronchitis, and arthritis; which comprises administering an effective amount of the composition defined in claim 15.

34. A method for the treatment of one or more virus-induced and autoimmune diseases selected from the group consisting of: diabetes mellitus, psoriasis, multiple sclerosis, viral eye disease, asthma, asthmatic bronchitis, and arthritis; which comprises administering an effective amount of the composition defined in claim 16.

35. A method for the treatment of one or more virus-induced and autoimmune diseases selected from the group consisting of: diabetes mellitus, psoriasis, multiple sclerosis, viral eye disease, asthma, asthmatic bronchitis, and arthritis; which comprises administering an effective amount of the composition defined in claim 17.

36. A method for the treatment of one or more virus-induced and autoimmune diseases selected from the group consisting of: diabetes mellitus, psoriasis, multiple sclerosis, viral eye disease, asthma, asthmatic bronchitis, and arthritis; which comprises administering an effective amount of the composition defined in claim 18.

37. A method for the treatment of one or more virus-induced and autoimmune diseases selected from the group consisting of: diabetes mellitus, psoriasis, multiple sclerosis, viral eye disease, asthma, asthmatic bronchitis, and arthritis; which comprises administering an effective amount of the composition defined in claim 19.

* * * * *